United States Patent
Kennedy et al.

(10) Patent No.: US 7,520,382 B2
(45) Date of Patent: *Apr. 21, 2009

(54) SUTURE PACKAGING (75) Inventors: Jack Kennedy, Guilford, CT (US); David Kirsch, Madison, CT (US); Michael Prescott, Hamden, CT (US)

(73) Assignee: Tyco Healthcare Group LP, Norwalk, CT (US)

(*) Notice: Subject to any disclaimer, the term of this patent is extended or adjusted under 35 U.S.C. 154(b) by 149 days.

This patent is subject to a terminal disclaimer.

(21) Appl. No.: 10/891,604

(22) Filed: Jul. 15, 2004

(65) Prior Publication Data

US 2005/0035007 A1 Feb. 17, 2005

Related U.S. Application Data (60) Provisional application No. 60/488,464, filed on Jul. 18, 2003.

(51) Int. Cl.
A61B 17/06 (2006.01)

(52) U.S. Cl. ..................... 206/63.3; 206/380

(58) Field of Classification Search ............... 206/63.3, 206/438, 574
See application file for complete search history.

(56) References Cited

U.S. PATENT DOCUMENTS

| | | | |
|---|---|---|---|
| 3,127,992 A | 4/1964 | Horine | |
| 4,243,140 A | 1/1981 | Thrun | |
| 4,424,898 A | 1/1984 | Thyen et al. | |
| 4,582,196 A * | 4/1986 | Hughson et al. | 206/63.3 |
| 4,699,271 A | 10/1987 | Lincoln et al. | |
| 4,961,498 A | 10/1990 | Kalinski et al. | |
| 4,967,902 A | 11/1990 | Sobel et al. | |
| 5,052,551 A | 10/1991 | Cerwin et al. | |
| 5,056,658 A * | 10/1991 | Sobel et al. | 206/63.3 |
| 5,099,994 A * | 3/1992 | Kalinski et al. | 206/409 |
| 5,121,836 A | 6/1992 | Brown et al. | |
| 5,131,533 A | 7/1992 | Alpern | |
| 5,154,283 A | 10/1992 | Brown | |
| 5,165,217 A | 11/1992 | Sobel et al. | |
| 5,179,818 A | 1/1993 | Kalinski et al. | |
| 5,180,053 A | 1/1993 | Cascio et al. | |
| 5,192,483 A | 3/1993 | Kilgrow et al. | |
| 5,197,597 A | 3/1993 | Leary et al. | |
| 5,213,210 A | 5/1993 | Cascio et al. | |

(Continued)

FOREIGN PATENT DOCUMENTS

EP 0 418 059 3/1991

(Continued)

OTHER PUBLICATIONS

European Search Report for EP 07007113.9-2310 date of completion is May 23, 2008 (8 pages).

Primary Examiner—Jacob K Ackun, Jr.

(57) ABSTRACT

A package for surgical suture material includes a base member and a cover member, wherein the cover member is configured to be placed adjacent to the base member to form the package for the surgical suture material. The base member includes an outer wall extending from an outer circumference thereof. The outer wall has a predetermined height such that it engages the cover member when the cover member is placed adjacent the base member. Partition structure extends from a bottom surface of the cover member and defines at least one suture retaining area.

6 Claims, 11 Drawing Sheets

U.S. PATENT DOCUMENTS

| | | | |
|---|---|---|---|
| 5,222,978 A | 6/1993 | Kaplan et al. | |
| 5,228,565 A | 7/1993 | Sinn | |
| 5,230,424 A | 7/1993 | Alpern et al. | |
| 5,236,083 A | 8/1993 | Sobel et al. | |
| 5,246,104 A | 9/1993 | Brown et al. | |
| 5,249,671 A | 10/1993 | Sinn | |
| 5,249,673 A | 10/1993 | Sinn | |
| 5,263,585 A | 11/1993 | Lawhon et al. | |
| 5,271,495 A * | 12/1993 | Alpern | 206/63.3 |
| 5,284,240 A | 2/1994 | Alpern et al. | |
| 5,350,060 A | 9/1994 | Alpern et al. | |
| 5,359,831 A | 11/1994 | Brown et al. | |
| 5,407,071 A | 4/1995 | Lawhon et al. | |
| 5,417,036 A | 5/1995 | Brown | |
| 5,462,162 A | 10/1995 | Kaplan et al. | |
| 5,468,252 A | 11/1995 | Kaplan et al. | |
| 5,472,081 A | 12/1995 | Kilgrow et al. | |
| 5,503,266 A * | 4/1996 | Kalbfeld et al. | 206/63.3 |
| 5,575,382 A | 11/1996 | Sobel et al. | |
| 5,628,395 A | 5/1997 | Daniele et al. | |
| 5,655,652 A | 8/1997 | Sobel et al. | |
| 5,669,490 A | 9/1997 | Colligan et al. | |
| 5,675,961 A | 10/1997 | Cerwin et al. | |
| 5,695,138 A | 12/1997 | Demarest et al. | |
| 5,704,469 A | 1/1998 | Daniele et al. | |
| 5,733,293 A | 3/1998 | Scirica et al. | |
| 5,788,062 A * | 8/1998 | Cerwin et al. | 206/63.3 |
| 5,833,055 A * | 11/1998 | Cerwin et al. | 206/63.3 |
| 5,887,706 A | 3/1999 | Pohle et al. | |
| 5,906,273 A | 5/1999 | Pohle et al. | |
| 5,918,733 A | 7/1999 | Cerwin et al. | |
| 6,016,905 A | 1/2000 | Gemma et al. | |
| 6,047,815 A | 4/2000 | Cerwin et al. | |
| 6,076,659 A * | 6/2000 | Baumgartner et al. | 206/63.3 |
| 6,098,796 A | 8/2000 | Januzeli et al. | |
| 6,105,339 A | 8/2000 | Pohle et al. | |
| 6,135,272 A * | 10/2000 | Sobel et al. | 206/63.3 |
| 6,135,385 A * | 10/2000 | Martinez de Lahidalga | 242/588.3 |
| 6,138,440 A | 10/2000 | Gemma | |
| 6,254,616 B1 | 7/2001 | Wright | |
| 6,260,699 B1 | 7/2001 | Kaplan et al. | |
| 6,394,269 B1 | 5/2002 | Rudnick et al. | |
| 6,464,071 B2 | 10/2002 | Baumgartner | |
| 6,481,568 B1 | 11/2002 | Cerwin et al. | |
| 6,481,569 B1 | 11/2002 | Alpern | |
| 6,533,112 B2 | 3/2003 | Warnecke | |
| 6,644,469 B2 * | 11/2003 | Alpern | 206/63.3 |
| 2003/0010655 A1 * | 1/2003 | Alpern | 206/63.3 |
| 2005/0035007 A1 | 2/2005 | Kennedy et al. | |

FOREIGN PATENT DOCUMENTS

| | | |
|---|---|---|
| EP | 0 558 085 | 9/1993 |
| EP | 0 558 086 | 9/1993 |
| EP | 0 726 062 | 8/1996 |
| EP | 0 728 445 | 8/1996 |
| EP | 0 564 274 | 5/1997 |
| EP | 0 914 802 A | 5/1999 |
| EP | 1093759 A | 4/2001 |
| EP | 1214912 A | 6/2002 |
| EP | 1 275 343 | 1/2003 |

* cited by examiner

SUTURE PACKAGING

CROSS-REFERENCE TO RELATED APPLICATIONS

This application claims the benefit of U.S. Provisional Patent Application No. 60/488,464 filed Jul. 18, 2003, the entire disclosure of which is hereby incorporated by reference herein."

BACKGROUND

1. Technical Field

The present disclosure relates to packages for surgical sutures, and more particularly to methods and apparatus for packaging surgical sutures.

2. Discussion of Related Art

A common form of surgical suture package is made of a folded stiff treated paper suture holder contained in a sterile, hermetically sealed envelope. This envelope is further sealed in a second, usually clear, thermoplastic heat-sealed envelope outer wrap to maintain the sterility of suture holder and inner envelope. When the suture is to be used, the outer clear wrap is opened, typically in the operating room, and the sealed sterile inner envelope is placed in a sterile area. Operating room personnel then open the inner envelope when access to the suture is needed.

Packages for surgical sutures having needles attached at one or both ends are constructed according to the nature of the suture material and to how the sutures will be used. Generally, the package holds the suture and attached needles in place, protects them during handling and storage, and allows ready access to the suture for removal with minimum handling at the time the suture is to be used.

An important aspect of the design and manufacture of suture packages is that the suture should be removable without becoming entangled with itself, kinked, coiled or bound in undesired ways. The nature of the suture material itself may impose limitations on the configuration of the package, how the suture is placed within the package, the placement of the needles, or how the suture is drawn from the package.

An exemplary packaging for surgical suture material is disclosed in U.S. Pat. No. 6,076,659. The '659 patent discloses a packaging for surgical suture material which has a base from which a wall extends in a spiral manner. The wall defines a suture duct within the area defined by the base. The suture duct opens at its first end into a suture-removal area. A cover is located above the suture duct. The spiral wall is provided on its outward-facing side with suture-deflector protrusions spaced apart from one another in the course of the suture duct.

A drawback in the case of the previously known packaging for surgical suture material is that, when the surgical suture material is being removed, the suture can pull tight in the suture retaining area in which it is guided over several spiral turns. That is, in the attempt to remove the suture from the packaging, the direction of the pulling force often causes the suture to move toward locations within the packaging which could cause the suture to become bound.

For example, the suture can move within the suture retaining area into an area which is formed by a junction between the wall extending like a spiral and the cover. The suture retaining area is defined by the spiral wall, the base and the cover. However, the wall in the suture package in the '659 patent, as well as many other prior art suture packages, extends from the bottom of the package toward the cover. Thus, a gap is frequently formed at a location which is defined by the junction of the wall and the cover. It is not uncommon for the suture to become wedged in the gap, thereby making further removal of the surgical suture material much more difficult or impossible.

The ability to readily access sutures and efficiently retrieve the sutures from their packaging is of utmost importance, especially when time is of the essence during a surgical procedure. Although apparatus and methods that adequately provide packaging for surgical suture material are known, the problems associated with the sutures becoming bound or otherwise caught within the suture package have not been entirely eliminated. Thus, a continuing need exists for improved suture packages which virtually eliminate any possibility of the suture becoming entangled or caught within the suture package.

SUMMARY

An object of the disclosure is to further develop a packaging for surgical suture material in such a way that surgical suture material situated in the packaging can be removed without problems. Accordingly, the present disclosure provides novel methods and apparatus for surgical suture packaging that eliminate many problems associated with the prior art suture packages.

A package for surgical suture material, in accordance with the present disclosure, includes a base member and a cover member, wherein the cover member is configured to be placed adjacent to the base member to form the package for the surgical suture material. The base member includes an outer wall extending from an outer circumference thereof. The outer wall has a predetermined height such that it engages the cover member when the cover member is placed adjacent the base member. Partition structure extends from a bottom surface of the cover member and retains the structure in a desired orientation within the package. The partition structure may include a plurality of protrusions displaced radially from a center of the cover. Additionally, an inner wall that extends from a bottom surface of the cover to define an inside edge of the suture retaining area may be provided in addition to or in place of the plurality of protrusions, to retaining the suture in a desired orientation within the package.

It is another aspect of the present disclosure to provide a surgical suture package which provides advantages and simplifies the manufacturing and winding processes.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

DETAILED DESCRIPTION OF PREFERRED EMBODIMENTS

Preferred embodiments of the presently disclosed suture package and method therefor will now be described in detail with reference to the figures, in which like reference numerals identify corresponding elements throughout the several views.

Figure 1A:
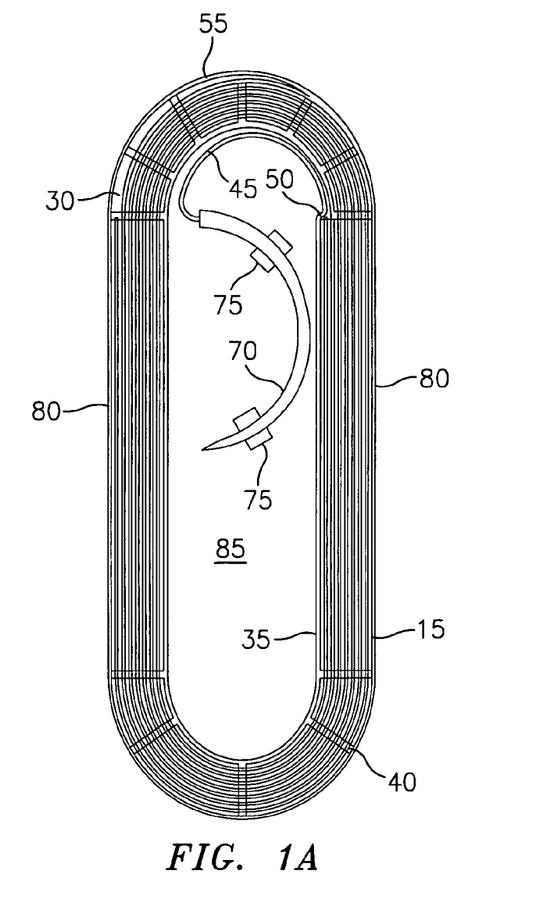
FIG. 1A is a top view of an embodiment of a suture package in accordance with an embodiment of the present disclosure.
Figure 1B:
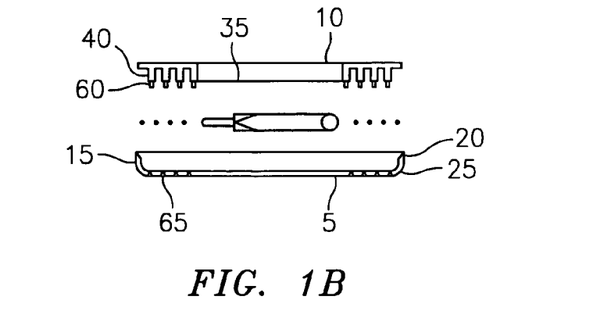
FIG. 1B is a side cross-sectional view of the suture package illustrated in FIG. 1A.

Referring now to FIGS. 1A and 1B, there is shown a top view and a side cross-sectional view, respectively, of an embodiment of a suture package in accordance with an embodiment of the present disclosure. The package has a base 5 and a cover 10. An outside wall 15 rises from base 5 and extends like an oval around a circumference of base 5. Outside wall 15 has an upper rim 20 and a lower rim 25. Lower rim 25 is connected to the base 5. Outside wall 15 is designed having a predetermined height such that upper rim 20 engages cover 10, preferably at the circumference thereof. Thus, when base 5 and cover 10 are moved adjacent each other, the outer circumference of cover 10 is joined with the upper rim 20 of outside wall 15 to form an outer wall of the closed suture package.

A suture retaining area 30 is defined on an outer boundary by outside wall 15, and on an inner boundary by an inner or interior wall 35. In accordance with an embodiment of the present disclosure, interior wall 35 preferably extends downward from cover 10. Unlike outside wall 15, interior wall 35 is not a continuous loop. Instead, interior wall 35 has a first end and a second end which will be described in further detail below. Adjacent to the first end of interior wall 35, an opening is defined which allows a first end of a suture 45 to enter into the suture retaining area 30. Interior wall 35 is also configured to follow the shape of the suture retaining area 30. Thus, at the point of the opening formed by interior wall 35, the end of the interior wall 35 is offset from any other portion of interior wall 35. This offset is necessary to maintain the shape of the suture retaining area 30 and to provide an opening for the suture 45 to access the suture retaining area 30.

Alternatively, it is contemplated that interior wall 35 may define an outer boundary of a plateau region in the center of cover 10. The height of the plateau region (also referred to as suture-removal area 85) is configured to be equivalent to the height of suture retaining area protrusions 40 less the thickness of a needle 70. Accordingly, a needle 70 may be positioned on the plateau in suture-removal area 85, on the outside surface of cover 10. In the case wherein it is desired to park the needle on the exterior of the suture package, a spacer may be placed on the plateau in suture-removal area 85. In an alternative embodiment, interior wall 35 defines an oval opening within cover 10. In that case, it is preferred that a needle park 75 is attached to base 5 within the suture-removal area 85. Therefore, surgical personnel have the ability to access and remove needle 70 through the opening within cover 10.

Extending downward from cover 10 is structure that partitions the suture package into one or more suture retaining areas. More specifically, a plurality of sets of four suture retaining area protrusions 40 defines a corresponding number of suture retaining areas. The sets of suture retaining area protrusions 40 are displaced radially from a center of the cover 10. It is also contemplated that the sets of suture retaining area protrusions may be configured as more or less than four retaining area protrusions such that more or less suture retaining areas are defined. Additionally, it is contemplated that the suture retaining area protrusions may be configured as one or more continuous walls which define one or more suture retaining areas.

Suture retaining area protrusions 40 are elongated finger members having a height which is substantially equivalent to the height of outside wall 15. Suture retaining area protrusions 40 are connected on a first end to the bottom surface of cover 10. A second end of suture retaining area protrusions 40 has a post 60 extending therefrom. Posts 60 are dimensioned to fit within holes 65 which are formed in base 5. Holes 65 may also be dimples or recesses. Posts 60 may also be heat staked or otherwise welded to base 5 to secure the cover 10 to the base 5. As cover 10 and base 5 are joined together, posts 60 extending from suture retaining area protrusions 40 engage holes 65 which are defined by base 5. This arrangement provides structural support to the suture package. The ends of the protrusions 40 may, alternatively, be deformed in the manner of rivets after the cover 10 has been fitted onto the base 5 with the wall 15. Other and/or additional types of connection between the wall 15 and the cover 10 are possible. Thus, e.g., the use of catches, which project at the periphery of the cover 10 and engage with suitable counterparts at the wall 15, is conceivable.

Also, as a result of the fit between the suture retaining area protrusions 40 and the holes 65 in base 5, the possibility of a surgical suture sticking in the region wherein the suture retaining area protrusions 40 meet base 5, as the suture is being removed from the packaging, is reliably avoided.

More specifically, since, in a particularly useful embodiment, the suture is removed through the cover, there will be a tendency for the suture to move in the direction of the cover 10, which is away from any gap which may form at the junction of the suture retaining area protrusions 40 and base 5. Thus, this configuration will further an objective of this disclosure, that is, to increase the reliability of the removability of the suture. Although the alternative embodiments described herein include various structural differences, a common feature of each of the embodiments is that the structure which forms the suture retaining areas extends from a bottom surface of the cover.

The suture retaining area protrusions 40 define the suture retaining areas 30 on the bottom of cover 10. The embodiment illustrated in FIGS. 1A and 1B includes a plurality of sets of four suture retaining area protrusions 40 extending radially outward between interior wall 35 and outside wall 15. Thus, a suture retaining area 30 defines and provides for four revolutions of suture 45. Also, in this embodiment, the suture retaining area protrusions 40 are only positioned in the end sections of the suture package. The two straight sides 80 of the suture package do not contain any protrusions. Thus, suture 45 is not restrained within defined retaining areas as the suture traverses each of the two sides 80.

A first end 50 of the suture retaining area 30 opens into a suture-removal area 85 which, in the embodiments illustrated in FIGS. 1A and 1B is arranged in the zone surrounded by the suture retaining area 30. The second end 55 of the suture retaining area 30 is closed, see FIG. 1A. The suture retaining area 30 is closed to the bottom by base 5.

Prior to being placed within a suture package, the suture is typically attached to a needle to provide a suture-needle combination. That is, a needle 70 is fitted onto an end of the suture 45. A needle park assembly 75 is provided within the central section of the suture-removal area 5 on an outer surface of cover 10 or an inner surface of base 5. The structure of needle park assembly 75 may be known to one having ordinary skill in the art. See, for example, U.S. Pat. Nos. 6,481,569, 5,788,062, 5,472,081, 5,180,053, 5,131,533, 5,099,994, and 4,424,898. It is contemplated that cover 10 includes an opening which permits free access to the suture-removal area 85. The opening may be a partial opening in the cover, or a more extensive opening, the advantages of each of which will be described below. Surgical personnel can gain access to the needle and suture through the opening in cover 10 and remove the needle suture combination by disengaging needle 70 from needle park 75 and then pulling the suture 45 from suture retaining area 30. It is to be noted that the needle 70 is positioned within the inner space defined by the suture 45. This configuration further assists in the removal of the needle-suture combination from the package.

Figure 1C:
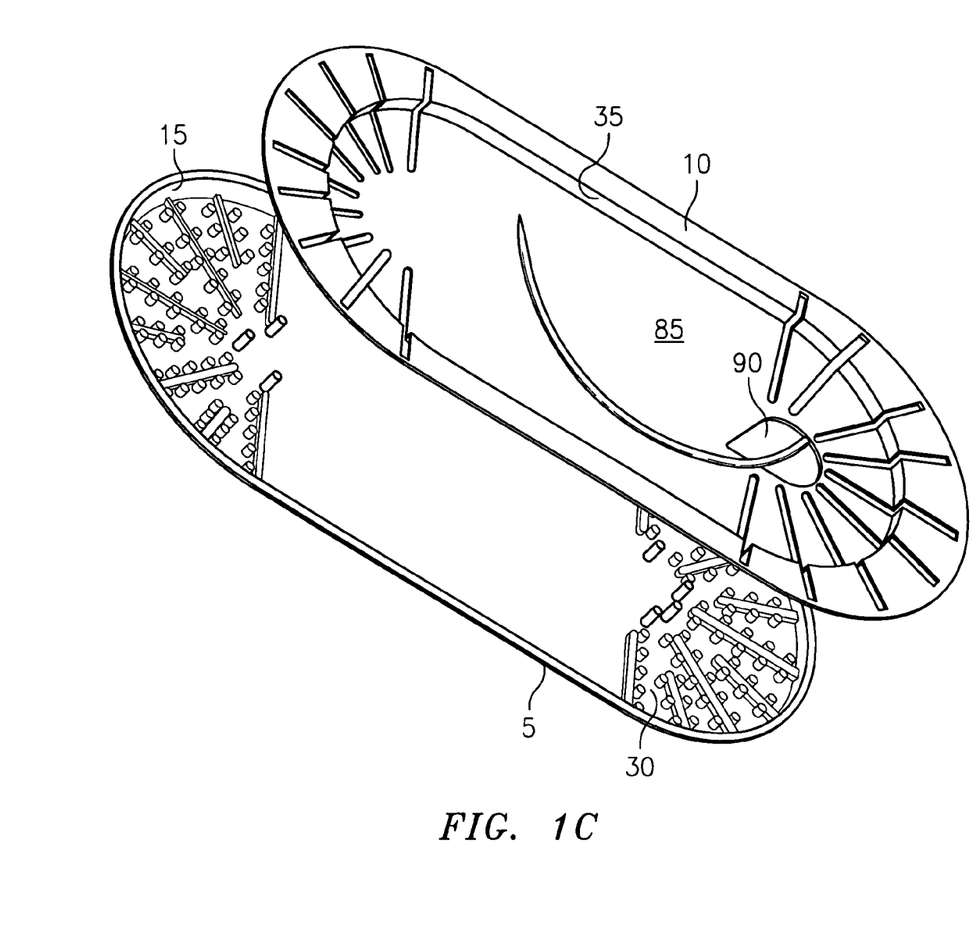
FIG. 1C is a perspective view of a suture package in accordance with an embodiment of the present disclosure.

FIG. 1C illustrates a perspective view of an embodiment of a suture package in accordance with the present disclosure. Illustrated in FIG. 1C are base 5 and cover 10. A needle 70 is shown positioned within a recessed suture-removal area 85 of cover 10. Thus, needle 70 is positioned on an exterior surface of the suture package. It is also contemplated that needle 70 may reside on base 5. In that case, the needle 70 may be retrieved from the suture package through an opening defined in cover 10 which is larger than opening 90.

Suture-removal area 85 is defined on an outer circumference by interior wall 35 which extends from a bottom surface of cover 10. Also extending from the bottom surface of cover 10 is a plurality of suture retaining area protrusions 40. When cover 10 is placed against base 5, suture retaining area protrusions 40 engage holes 65 formed in base 5.

As discussed with reference to FIGS. 1A and 1B, a suture retaining area 30 is defined on an outer boundary by outside wall 15, and an inner boundary by interior wall 35. At the end portion of the suture package, suture retaining area 30 is divided into two or more separate retaining areas by suture retaining area protrusions 40.

Figure 2A:
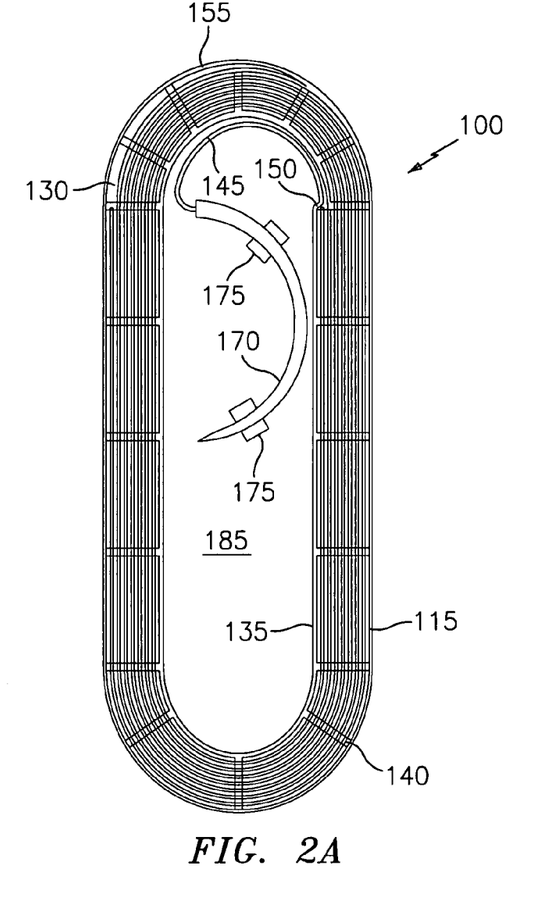
FIG. 2A is a top view of an embodiment of a suture package in accordance with an embodiment of the present disclosure.
Figure 2B:
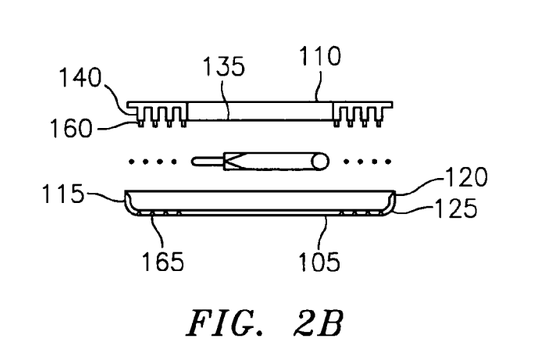
FIG. 2B is a side cross-sectional view of the suture package illustrated in FIG. 2A.

Referring now to FIGS. 2A and 2B, there is shown a top view and a side cross-sectional view, respectively, of an embodiment of a suture package 100 in accordance with an embodiment of the present disclosure. The package has a base 105 and a cover 110. An outside wall 115 rises from base 105 and extends like an oval around a circumference of base 105. Outside wall 115 has an upper rim 120 and a lower rim 125. Lower rim 125 is connected to the base 105. Outside wall 115 is designed having a predetermined height such that upper rim 120 engages cover 110, preferably at the circumference thereof. Thus, when base 105 and cover 110 are moved adjacent each other, the outer circumference of cover 110 is joined with the upper rim 120 of outside wall 115 to form an outer wall of the closed suture package 100.

A suture retaining area 130 is defined on an outer boundary by outside wall 115, and on an inner boundary by an inner or interior wall 135. In accordance with an embodiment of the present disclosure, interior wall 135 preferably extends downward from cover 110. Unlike outside wall 115, interior wall 135 is not a continuous loop. Instead, interior wall 135 has a first end and a second end which will be described in further detail below. Adjacent to the first end of interior wall 135, an opening is defined which allows a first end of a suture 145 to enter into the suture retaining area 130. Interior wall 135 is also configured to follow the shape of the suture retaining area 130. Thus, at the point of the opening formed by interior wall 135, the end of the interior wall 135 is offset from any other portion of wall 135. This offset is necessary to maintain the shape of the suture retaining area 130 and to provide an opening for the suture 145 to access the suture retaining area 130.

Extending downward from cover 110 is structure which partitions the suture package into one or more suture retaining areas. More specifically, a plurality of sets of four suture retaining area protrusions 140 defines a corresponding number of suture retaining areas. The sets of suture retaining area protrusions 140 are displaced radially from a center of the cover 105. It is also contemplated that the sets of suture retaining area protrusions may be configured as more or less than four retaining area protrusions such that more or less suture retaining areas are defined. Additionally, it is contemplated that the suture retaining area protrusions may be configured as one or more continuous walls which define one or more suture retaining areas.

Suture retaining area protrusions 140 are elongated finger members having a height which is substantially equivalent to the height of outside wall 115. Suture retaining area protrusions 140 are connected on a first end to the bottom surface of cover 110. A second end of suture retaining area protrusion 140 has a post 160 extending therefrom. Posts 160 are dimensioned to fit within holes 165 which are formed in base 105. Holes 165 may also be dimples or recesses. Posts 160 may also be heat staked or otherwise welded to base 105 to secure the cover 110 to the base 105. As cover 110 and base 105 are joined together, posts 160 extending from suture retaining area protrusions 140 engage holes 165 which are defined by base 105. This arrangement provides structural support to the suture package. The ends of the protrusions 140 may, alternatively, be deformed in the manner of rivets after the cover 110 has been fitted onto the base 105 with the wall 115. Other and/or additional types of connection between the wall 115 and the cover 110 are possible. Thus, e.g., the use of catches, which project at the periphery of the cover 110 and engage with suitable counterparts at the wall 115, is conceivable.

Also, as a result of the fit between the suture retaining area protrusions 140 and the holes 165 in base 105, the possibility of a surgical suture sticking in the region wherein the suture retaining area protrusions 140 meet base 105, as the suture is being removed from the packaging, is reliably avoided.

More specifically, since, in the preferred embodiment, the suture is removed through the cover, there will be a tendency for the suture to move in the direction of the cover 110, which is away from any gap which may form at the junction of the suture retaining area protrusions 140 and base 105. Thus, this configuration will further an objective of this embodiment, that is, to increase the reliability of the removability of the suture. Although the alternative embodiments described herein include various structural differences, a common feature of each of the embodiments is that the structure which forms the suture retaining areas extends from a bottom surface of the cover.

The suture retaining area protrusions 140 define the suture retaining areas 130 on the bottom of cover 110. The embodiment illustrated in FIGS. 2A and 2B includes a plurality of sets of four suture retaining area protrusions 140 extending radially outward between interior wall 135 and outside wall 115. Thus, a suture retaining area 130 defines and provides for four revolutions of suture 145.

A first end 150 of the suture retaining area 130 opens into a suture-removal area 185 which in the embodiments illustrated in FIGS. 2A and 2B is arranged in the zone surrounded by the suture retaining area 130. The second end 155 of the suture retaining area 130 is closed, see FIG. 2A. The suture retaining area 130 is closed to the bottom by base 105.

Prior to being placed within a suture package, the suture is typically attached to a needle to provide a needle-suture-combination. That is, a needle 170 is fitted onto an end of the suture 145. A needle park assembly 175 is provided within the central section of the suture-removal area 185 on an outer surface of cover 110 or an inner surface of base 105. Cover 110 includes an opening which permits free access to the suture-removal area 185. Surgical personnel can gain access to the needle and suture through the opening in cover 110 and remove the suture by disengaging needle 170 from needle park 175 and then pulling the suture 145 from suture retaining area 130. It is to be noted that the needle 170 is positioned within the inner space defined by the suture 145. This configuration further assists in the removal of the suture from the package.

Figure 3A:
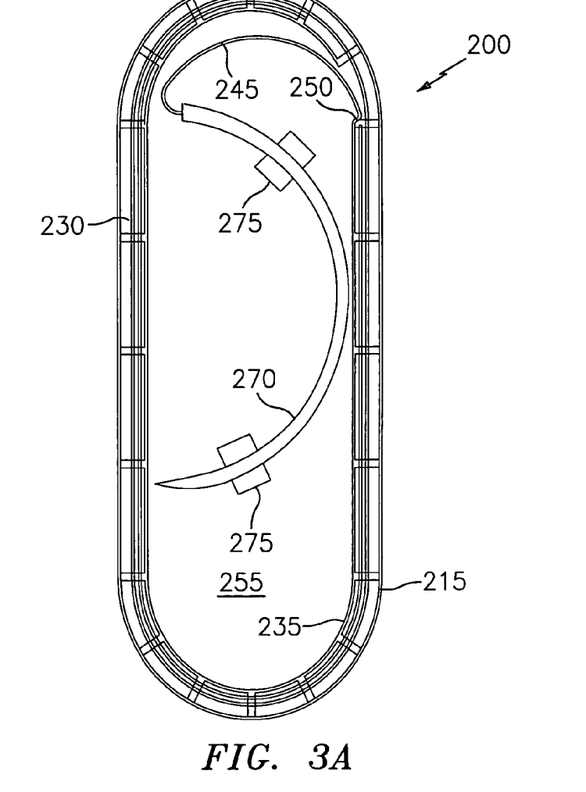
FIG. 3A is a top view of an embodiment of a suture package in accordance with an embodiment of the present disclosure.
Figure 3B:
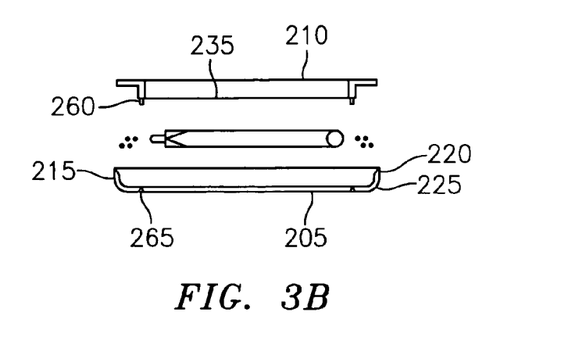
FIG. 3B is a side cross-sectional view of the suture package illustrated in FIG. 3A.

FIGS. 3A and 3B illustrate a top view and a side cross-sectional view, respectively, of an embodiment of a suture package 200 in accordance with another embodiment of the present disclosure. The package has a base 205 and a cover 210. An outside wall 215 rises from base 205 and extends like an oval around a circumference of base 205. Outside wall 215 has an upper rim 220 and a lower rim 225. Lower rim 225 is connected to the base 205. Outside wall 215 is designed having a predetermined height such that upper rim 220 engages cover 210, preferably at the circumference thereof. Thus, when base 205 and cover 210 are moved adjacent each other, the outer circumference of cover 210 is joined with the upper rim 220 of outside wall 215 to form an outer wall of the closed suture package 200.

An oval suture retaining area 230 is defined on an outer boundary by outside wall 215, and on an inner boundary by an interior wall 235. In accordance with an embodiment of the present disclosure, interior wall 235 preferably extends downward from cover 210. Unlike outside wall 215, interior wall 235 is not a continuous loop. Instead, interior wall 235 has a first end 250 and a second end 255. Adjacent to the first end 250, an opening is defined which allows a first end of a suture 245 to enter into the oval suture retaining area 230. Additionally, a gap is maintained between the first and second ends 250, 255 to provide access of a needle 270 to a region in the center of the suture winding.

Interior wall 235 includes a plurality of posts 260 spaced apart and extending therefrom. The height of interior wall 235 is substantially equivalent to the height of outside wall 215. Posts 260 are dimensioned to fit within holes 265 which are formed in base 205. Holes 265 may also be dimples or recesses. Therefore, as cover 210 and base 205 are joined together, posts 260 extending from interior wall engage holes 265 which are defined by base 205. This arrangement provides structural support to the suture package. The posts 260 may, alternatively, be deformed in the manner of rivets after the cover 210 has been fitted onto the base 205 with the wall 215. Other and/or additional types of connection between the wall 215 and the cover 210 are possible. Thus, e.g., the use of catches, which project at the periphery of the cover 210 and engage with suitable counterparts at the wall 215, is conceivable.

Prior to being placed within a suture package, needle 270 is fitted onto an end of the suture 245. A needle park assembly 275 is provided within the central section of the suture-removal area 285 on the exterior surface of cover 210 or an inner surface of base 205. Cover 210 includes an opening which permits free access to the suture-removal area 285. Surgical personnel can gain access to the needle and suture through the opening in cover 210 and remove the suture by disengaging needle 270 from needle park 275 and then pulling the suture 245 from suture retaining area 230.

Figure 4A:
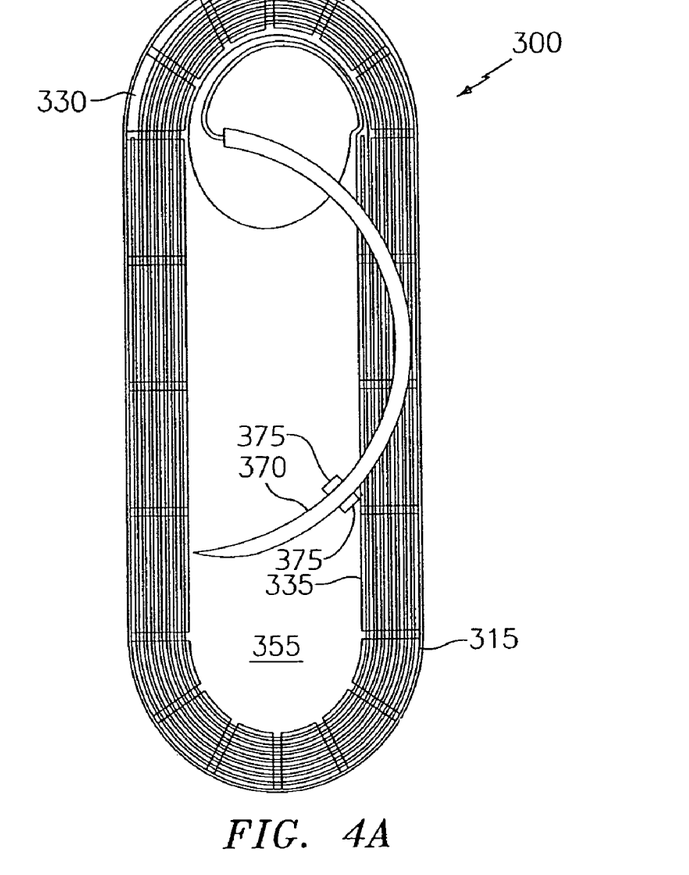
FIG. 4A is a top view of an embodiment of a suture package having an external needle park in accordance with an embodiment of the present disclosure.
Figure 4B:
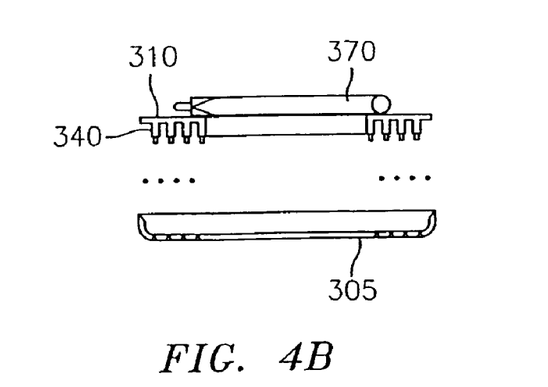
FIG. 4B is a side cross-sectional view of the suture package having an external needle park illustrated in FIG. 4A.

Referring now to FIGS. 4A and 4B, there is shown a top view and a side cross-sectional view, respectively, of an embodiment of a suture package 300 having an external needle park in accordance with an embodiment of the present disclosure. The suture package 300 is similar to the suture package described above with reference to FIGS. 2A and 2B with an exception being the location of the needle park. That is, instead of positioning the needle park assembly on the upper surface of base 305, within the central region defined by the suture winding retaining areas 330, the needle 370 and needle park assembly 375 are positioned on the upper surface of cover 310. This configuration makes the suture-needle combination more accessible to the surgical personnel. The surgical personnel would simply disengage the needle 370 from the needle park assembly 375 and apply a pulling force to pull the suture, which is attached to the needle.

A suture retaining area 330 is defined on an outer boundary by outside wall 315, and on an inner boundary by an interior wall 335, as described above with reference to FIGS. 2A and 2B. Interior wall 335 extends downward from cover 310. Also extending downward from cover 310 is a plurality of sets of four suture retaining area protrusions 340 to define a corresponding number of suture retaining areas.

Figure 5A:
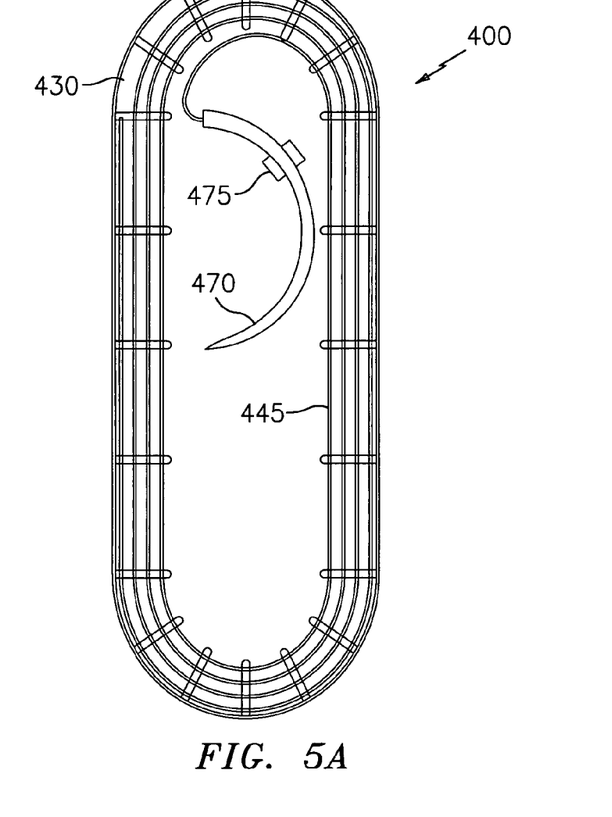
FIG. 5A is a top view of an embodiment of a suture package in accordance with an embodiment of the present disclosure.
Figure 5B:
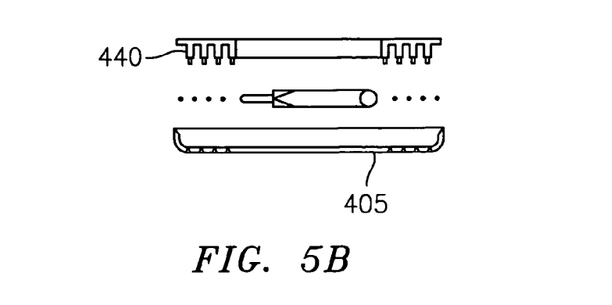
FIG. 5B is a side cross-sectional view of the suture package illustrated in FIG. 5A.

Referring now to FIGS. 5A and 5B, there is shown a top view and a side cross-sectional view, respectively, of an embodiment of a suture package 400 in accordance with an embodiment of the present disclosure. The suture package 400 is similar to the suture package described above with reference to FIGS. 2A and 2B with an exception being the absence of inner wall 135. That is, instead of having a contiguous inner wall defining the inner boundary of the suture retaining area 430, the inner boundary of suture retaining area 430 is defined by the plurality of suture retaining area protrusions 440. Suture 445 is wound within the suture retaining area 430 defined by suture retaining area protrusions 440. The needle 470 and needle park assembly 475 are positioned on the upper surface of base 405 within the central region defined by the suture retaining areas 430.

Figure 6A:
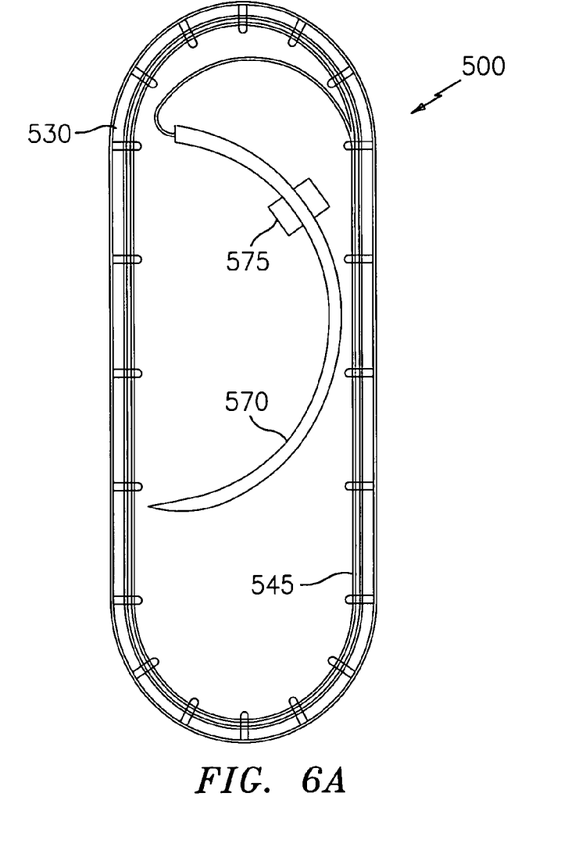
FIG. 6A is a top view of an embodiment of a suture package in accordance with an embodiment of the present disclosure.
Figure 6B:
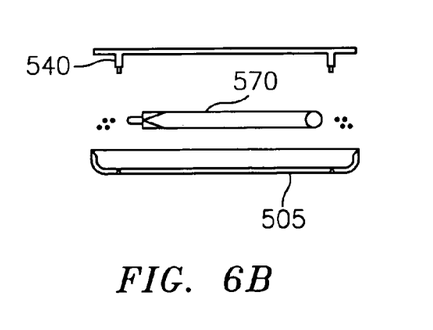
FIG. 6B is a side cross-sectional view of the suture package illustrated in FIG. 6A.

Referring now to FIGS. 6A and 6B, there is shown a top view and a side cross-sectional view, respectively, of an embodiment of a suture package 500 in accordance with an embodiment of the present disclosure. The suture package 500 is similar to the suture package described above with reference to FIGS. 3A and 3B with an exception being the absence of inner wall 235. That is, instead of having a contiguous inner wall defining the inner boundary of the suture retaining area 530, the inner boundary of suture retaining area 530 is defined by a plurality of suture retaining area protrusions 540. Suture 545 is wound within the suture retaining area 530 defined by suture retaining area protrusions 540. The needle 570 and needle park assembly 575 are positioned on the upper surface of base 505 within the central region defined by the suture winding retaining areas 530.

Figure 7A:
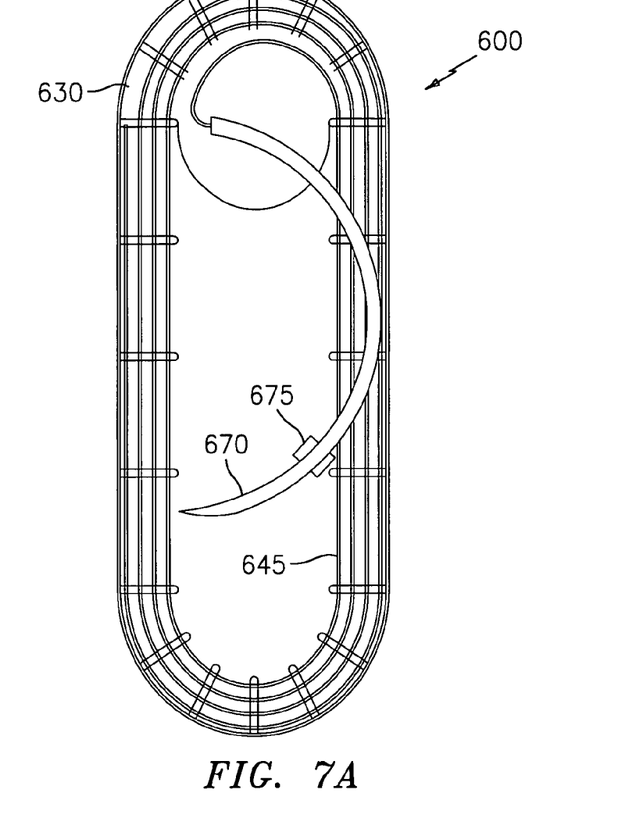
FIG. 7A is a top view of an embodiment of a suture package having an external needle park in accordance with an embodiment of the present disclosure.
Figure 7B:
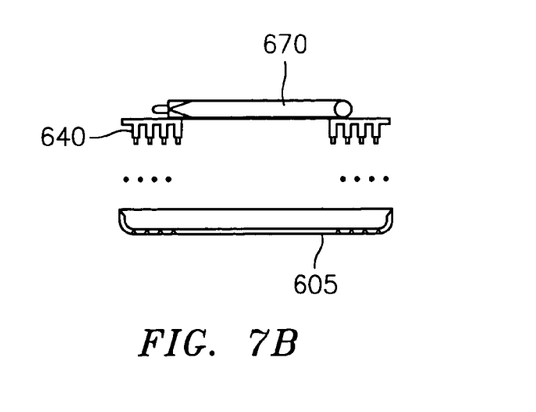
FIG. 7B is a side cross-sectional view of the suture package having an external needle park illustrated in FIG. 7A.

"Referring now to FIGS. 7A and 7B, there is shown a top view and a side cross-sectional view, respectively, of an embodiment of a suture package 600 in accordance with an embodiment of the present disclosure. The suture package 600, possessing a base 605 is similar to the suture package described above with reference to FIGS. 4A and 4B with an exception being the absence of inner wall 335. That is, instead of having a contiguous inner wall defining the inner boundary of the suture retaining area 630, the inner boundary of suture retaining area 630 is defined by the plurality of suture retaining area protrusions 640. Suture 645 is wound within the suture retaining area 630 defined by suture retaining area protrusions 640. The needle 670 and needle park assembly 675 are positioned on the upper surface of cover 610 within the central region defined by the suture retaining areas 630."

The packages described herein may be manufactured from conventional moldable materials. It is especially preferred to use polyolefin materials such as polyethylene and polypropylene, other thermoplastic materials, and polyester materials such as nylon, and equivalents thereof. Preferably, the presently described packages are injection molded, however, the packages may be formed by other conventional processes and equivalents thereof including thermo-forming. If desired, the packages may be manufactured as individual assemblies or components which are then assembled.

Figure 8:
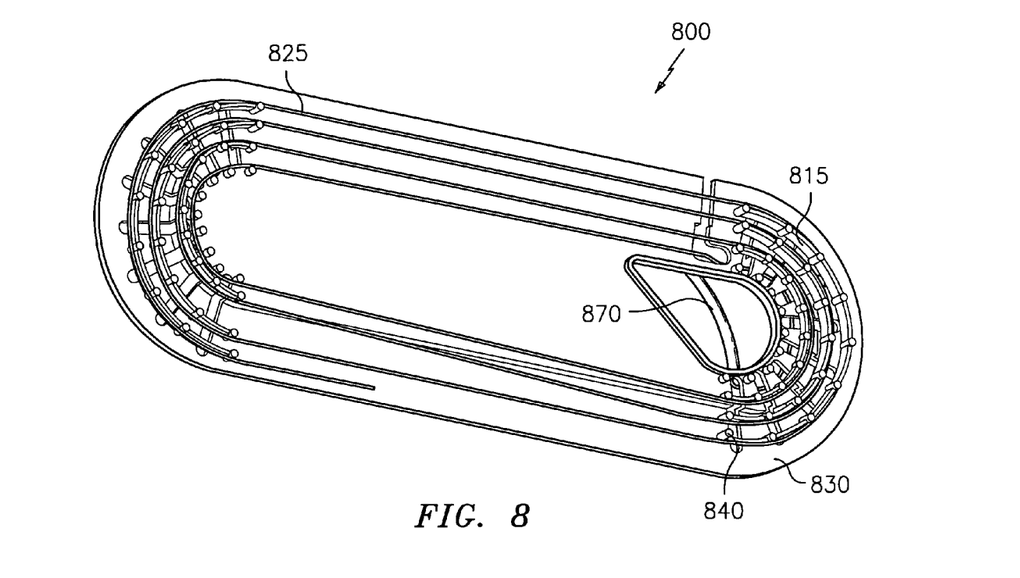
FIG. 8 is a perspective view of a suture package in accordance with an embodiment of the present disclosure.
Figure 9:
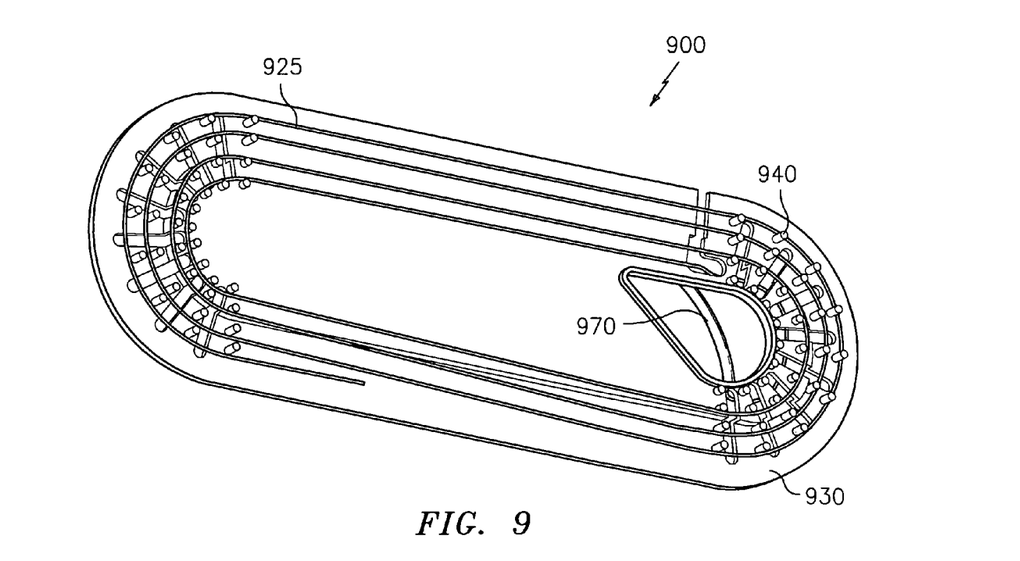
FIG. 9 is a perspective view of a suture package in accordance with an embodiment of the present disclosure.

FIGS. 8 and 9 are perspective views of suture packages in accordance with embodiments of the present disclosure. The suture packages 800 and 900, illustrated in FIGS. 8 and 9, respectively, are similar to each other and to the suture package described above with reference to FIG. 1C, with certain differences. The most significant difference is the addition of partitions 815 in the embodiment illustrated in FIG. 8. Partitions 815 connect each row of suture retaining area protrusions 840. Thus, instead of having individual suture retaining area protrusions 940, partitions 815 connect the suture retaining area protrusions 840 in a manner which defines a contiguous wall to further define suture retaining areas 830. Sutures 825 and 925 having needles 870 and 970 attached thereto are illustrated wound within suture retaining areas 830 and 930. The partitions 815 enhance the connection between the cover and base to prevent suture binding. Additionally, benefits associated with the injection molding process are realized with the embodiment having partitions.

Figure 10:
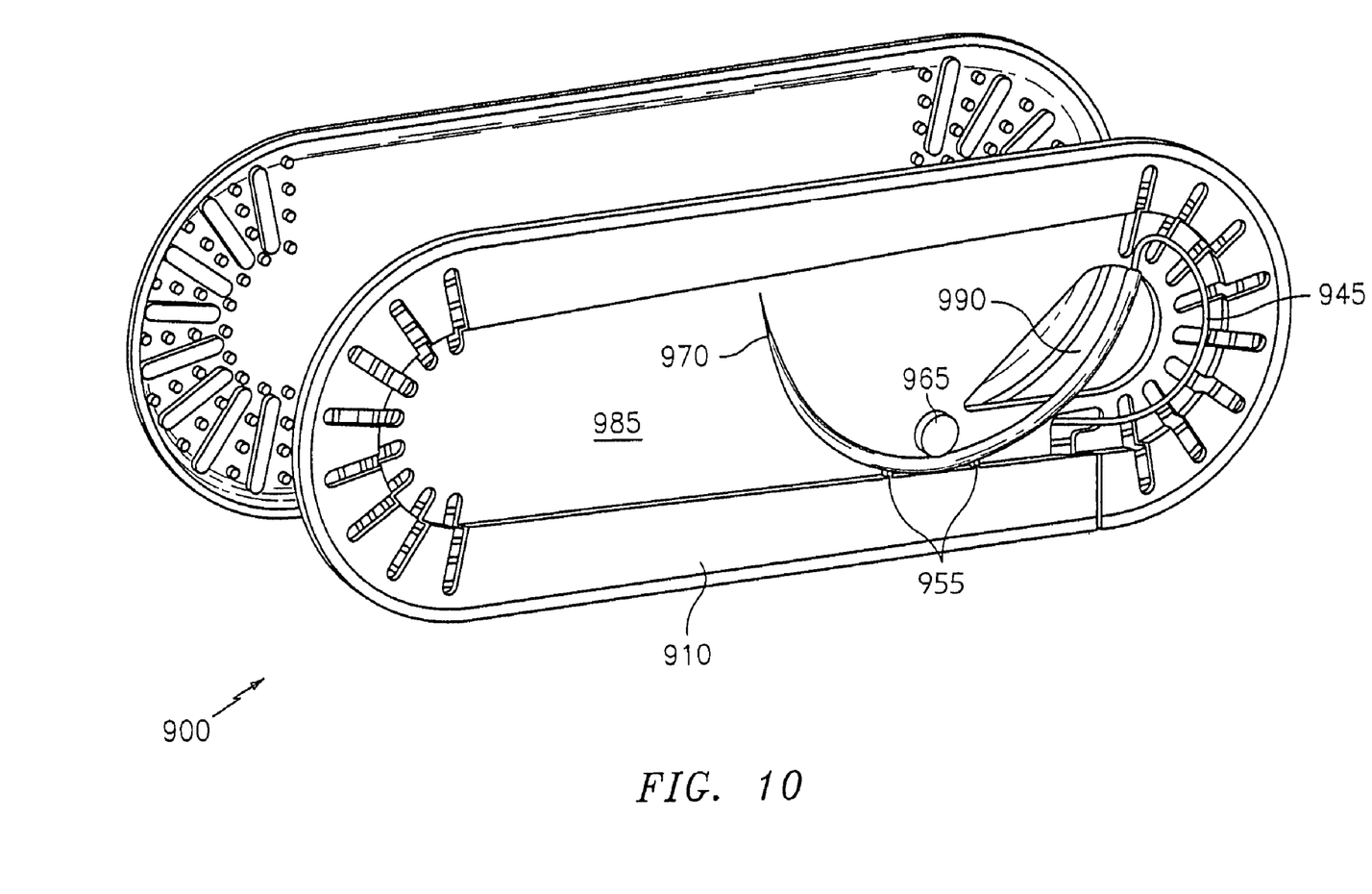
FIG. 10 is a perspective view of a suture package having a needle park in accordance with an embodiment of the present disclosure.

Referring now to FIG. 10, prior to being placed within a suture package, the suture is typically attached to a needle to provide a needle-suture combination. That is, a needle 970 is fitted onto an end of the suture 945. A needle park assembly 975 is provided within the central section of the suture-removal area 985 on a surface of cover 910. Needle park assembly 975 includes a pair of fins 955 and a post 965. Post 965 has a circular cross-section and fins 955 are flexible. Thus, in combination, the characteristics of fins 955 and post 965 provide a three-point contact with a needle 970 and allow needle park assembly 975 to accommodate needles having different curvatures.

It is contemplated that cover 910 defines an opening 990 to provide unrestricted access for surgical personnel to the needle 970. More specifically, opening 990 provides surgical personnel with the ability to insert a needle holder past the surface of the cover. Surgical personnel can gain access to the needle and suture through the opening 970 in cover 910 by disengaging needle 970 from needle park 975 and then pulling the suture 945 from suture retaining area.

Figure 11:
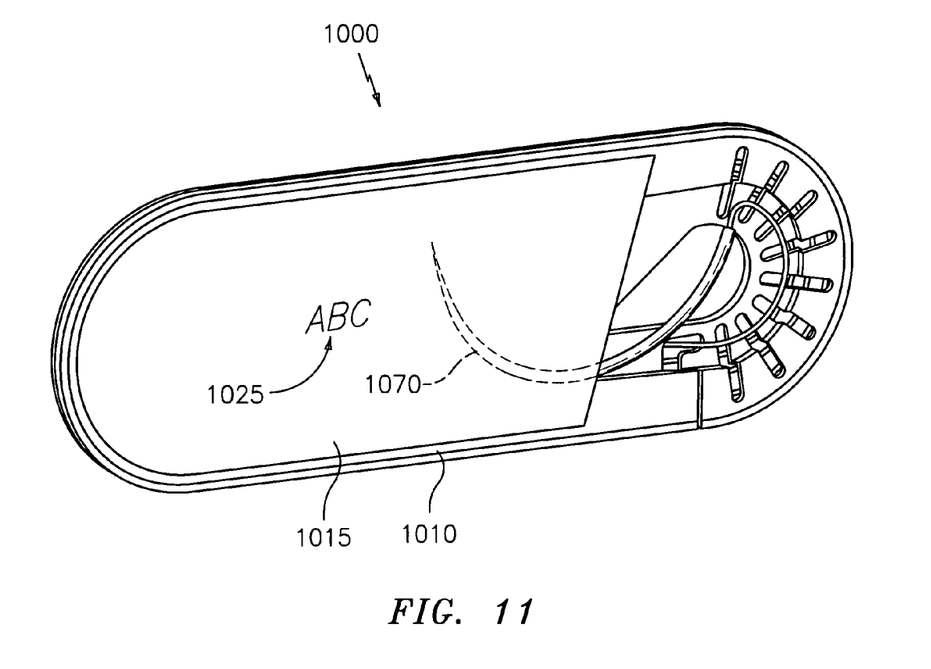
FIG. 11 is a perspective view of a suture package having an information label attached to an upper surface of the cover of the suture package in accordance with an embodiment of the present disclosure.

Referring now to FIG. 11, it is further contemplated that the assembled suture packaging 1000 is packed in a foil wrapper (not shown) as is known to one having ordinary skill in the art. Additionally, in a preferred embodiment, an information label 1015 is attached to an upper surface of the cover 1010. The information label 1015 includes indicia 1025 which, at least in part, provides information regarding the contents of the suture package. It is preferred that the information label 1015 is attached to the cover 1010 via an adhesive around at least a portion of a perimeter of the label. When applying the adhesive, care should be exercised to keep the adhesive from coming into contact with the needle and/or suture. Information label 1015 is preferably formed of paper. A paper label is particularly useful as a moisture sink when bio-absorbable sutures are used. Information label 1015 illustrated in FIG. 11 does not completely cover the entire surface area of cover 1010. Thus, the surgical personnel will have ready access to needle 1070 as well as the ability to quickly remove information label 1015.

Figure 12:
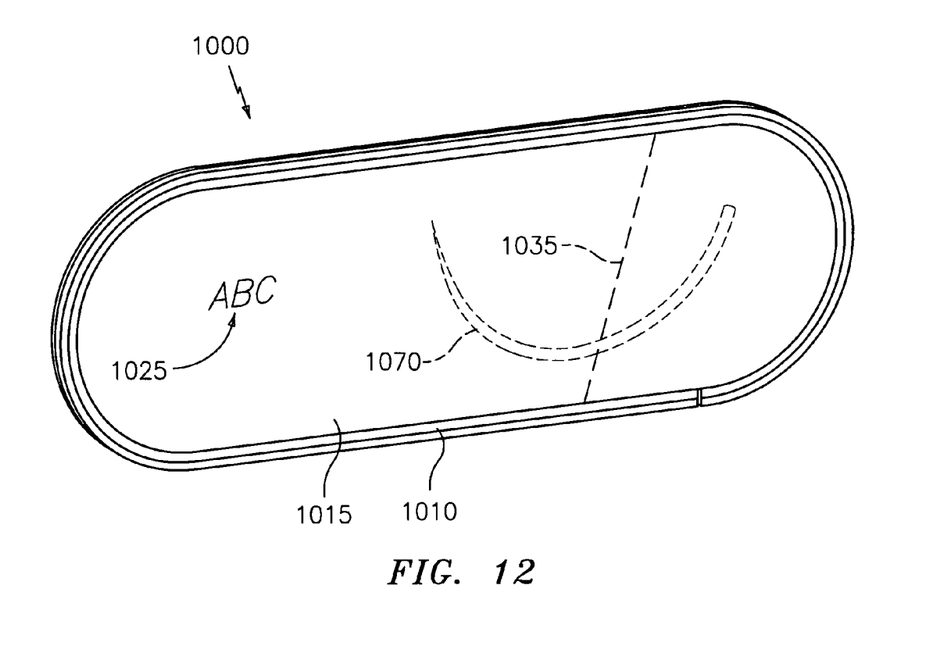
FIG. 12 is a perspective view of a suture package having an information label attached to an upper surface of the cover of the suture package in accordance with an embodiment of the present disclosure.

In contrast to the information label illustrated in FIG. 11, the information label 1015 illustrated in FIG. 12 covers the entire surface area of cover 1010. The paper information label 1015 includes a plurality of perforations 1035 to define a tear line in a predetermined location. The predetermined location corresponds to a location above and substantially perpendicular to the needle 1070 (shown in phantom) which is parked on the upper surface of the cover 1010. The perforations 1035 guide the tear when the surgical personnel open the package and prevent the needle from tipping.

It will be understood that various modifications may be made to the embodiments disclosed herein. For example, although the above embodiments are described with reference to a surgical suture package, it is contemplated that the disclosure is not limited to such an application and may be applied to various medical instruments. Additionally, although the illustrative embodiments described herein disclose a single needle-suture combination within the package, it is contemplated that multiple sutures may be housed within a single suture package. As yet another example, rather than mounting the needle park to a surface of the cover, the needle park can be located on a surface of the base. As yet another example, rather than removing the suture-needle combination through an opening in the cover, it is contemplated that the suture-needle combination can be removed through an opening formed in the base. Therefore, the above description should not be construed as limiting, but merely as exemplifications of preferred embodiments. Those skilled in the art will envision other modifications within the scope and spirit of the claims.

What is claimed is:

1. A suture package comprising:
   a base having an upwardly extending peripheral wall of a first height and an upper surface;
   a cover having a substantially planar edge portion terminating atop the peripheral wall and a downwardly extending inner wall of a second height substantially equivalent to the height of the peripheral wall;
   a suture retaining area defined between the peripheral wall and the inner wall; and a plurality of arcuate rows of posts extending downwardly from the cover and located between the peripheral wall and the inner wall, said posts extending from the cover to the planar upper surface of the base to define at least a portion of the suture retaining area, wherein each post has a third height that is substantially similar to the first height of the upwardly extending peripheral wall.

2. A suture package as in claim 1 further comprising a needle park.

3. A suture package as in claim 2 wherein the needle park is located on an upper surface of the cover.

4. A suture package as in claim 2 where in the needle park is located on the upper surface of the base.

5. A suture package as in claim 1 further comprising a needle and suture disposed therein wherein the cover includes an opening configured and dimensioned to allow access to the needle and suture.

6. A suture package as in claim 1 further comprising an information label attached to an upper surface of the cover.

\* \* \* \* \*